US00PP14082P39

(12) United States Plant Patent
Utecht

(10) Patent No.: US PP14,082 P3
(45) Date of Patent: Aug. 19, 2003

(54) GERANIUM PLANT NAMED 'FIP 336'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,734

(22) Filed: Sep. 30, 2002

(65) Prior Publication Data

US 2003/0101493 P1 May 29, 2003

(51) Int. Cl.[7] ..... A01H 5/00

(52) U.S. Cl. ..... Plt./325

(58) Field of Search ..... Plt./325

*Primary Examiner*—Kent Bell
(74) *Attorney, Agent, or Firm*—Foley & Lardner

(57) ABSTRACT

A new and distinct cultivar of geranium plant named 'Fip 336', characterized by the combined features of light-pink semi-double flowers with rose-red eyes, large umbels high above the foliage, deep green foliage without or with only weak zonation, moderately vigorous growth, bushy, round plant habit and medium to late spring flowering response.

1 Drawing Sheet

Latin name of the genus and species of the plant claimed: *Pelargonium zonale* L'Héritier.
Variety denomination: 'Fip 336'.

BACKGROUND OF THE INVENTION

The present invention comprises a new and distinct cultivar of geranium, botanically known as *Pelargonium zonale,* and hereinafter referred to by the cultivar name 'Fip 336'.

'Fip 336' is a product of a planned breeding program which had the objective of creating new zonal geranium cultivars with light pink flower color, semi-double flower type, intense green foliage and medium sized, well-branched plant habit.

'Fip 336' originated from a hybridization made by the inventor Angelika Utecht in a controlled breeding program in Galdar, Gran Canaria, Spain, in 1997.

The female parent was the commercial variety 'Tossa' (U.S. Plant Pat. No. 9,572), having light pink, semi-double flowers, medium green foliage with distinct zonation, and medium to moderately vigorous growth habit. The male parent of 'Fip 336' was the unpatented hybrid No. 96-1029-1, having bluish-pink, single-type flowers with distinct red eyes, foliage without zonation, and medium growth. This plant was derived from a cross between 'Fisblu' (U.S. Plant Pat. No. 9,764), and the commercial variety 'Azulia', unpatented.

'Fip 336' was selected as one flowering plant within the progeny of the stated cross by Angelika Utecht in 1998 in a controlled environment in Galdar, Gran Canaria, Spain. The first act of asexual reproduction of 'Fip 336' was accomplished when vegetative cuttings were taken from the initial selection in the fall of 1998 in a controlled environment in Galdar, Gran Canaria, Spain, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fip 336' are firmly fixed and are retained through successive generations of asexual reproduction.

'Fip 336' has not been observed under all possible environmental conditions. The phenotype may vary significantly with variations in environment such as temperature, light intensity and day length.

The following observations, measurements, and comparisons describe plants grown in Hillscheid, Germany under greenhouse conditions which approximate those generally used in commercial practice.

BRIEF SUMMARY OF THE INVENTION

The following traits have been repeatedly observed and are determined to be basic characteristics of 'Fip 336' and in combination distinguish this geranium as a new and distinct cultivar:

1. Light pink flower color with bright rose-red eyes;
2. large inflorescences, borne on strong peduncles high above the foliage;
3. intense medium-green foliage with very weak zonation;
4. moderately vigorous, bushy and rounded plant habit; and
5. medium to moderately late spring flowering response.

Of the many commercial cultivars known to the present inventor, the most similar in comparison to 'Fip 336' are the related variety 'Fisblu', and the variety 'Fiscaseye' (Copending U.S. Plant patent application No. 10/259,663).

In comparison to 'Fisblu', 'Fip 336' has a lighter pink ground color of flowers and grows much more vigorously. In comparison to 'Fiscaseye', the inflorescences of 'Fip 336' are bigger and distinctly higher above the foliage, and the plant habit of 'Fip 336' is generally somewhat taller. The pink ground color of the flowers is somewhat lighter, so is the color of the lower sides of petals and of the buds, while foliage color is a slightly deeper green.

BRIEF DESCRIPTION OF THE DRAWING

The accompanying photographic drawing shows typical flower and foliage characteristics of 'Fip 336' with colors being as true as possible with an illustration of this type. The drawing depicts a side elevational view of a typical potted flowering plant of 'Fip 336'.

DETAILED BOTANICAL DESCRIPTION

Measurements were taken in Hillscheid, Germany, in mid May 2002, about 10 weeks after planting of rooted cuttings. The plants were growing in 14 cm plastic pots and had not been pinched. In the following description color references are made to The Royal Horticultural Society Colour Chart. The color values were determined indoors from plants developed in a green-house in May 2002 in Hillscheid, Germany.

Inflorescence:
- *Type.*—Umbel, semi-spherically shaped.
- *Average diameter.*—125 mm.
- *Average depth.*—75 mm.
- *Peduncle length.*—225 mm.
- *Peduncle color.*—Green, RHS 143 B.
- *Pedicel length.*—28 mm.
- *Pedicel color.*—Green, RHS 143 B, brownish infused, RHS 179 A, at the upper end.
- *Number of flowers per umbel.*—About 30–35.

Corolla:
- *Average diameter.*—49 mm.
- *Form.*—Semi-double type.
- *Shape.*—Round outline, with the upper petals about the same size as the lower petals, cup-shape.
- *Number of petals.*—6–8.
- *Number of petaloids.*—0–2.
- *Shape of petals.*—Obovate, base acute, upper end is rounded, margin is entire.
- *Size of petals.*—Upper petals: 24–26 mm long, 24–26 mm wide; lower petals: 24–26 mm long, 23–25 mm wide.
- *Color (general tonality from a distance of three meters).*—Light pink with rose-red eyes.
- *Color of upper petals.*—Main part RHS 65 A, near margin 65 B, white base RHS 155 D.
- *Markings of upper petals.*—Very fine pink veins, reddish eyes, RHS 57 C.
- *Color of lower petals.*—Light pink, RHS 65 A.
- *Markings of lower petals.*—Rose-red eyes, RHS 57 B.
- *Color of lower surface of petals.*—Mainly RHS 62 D, near margin RHS 62 C.
- *Petaloids.*—Same color as petals.
- *Color of sepals.*—Upper surface: light green, RHS 143 B, base 179 B; lower surface: light green, RHS 143 C, base 179 B.
- *Number of sepals.*—5.
- *Shape of sepals.*—Linear to lanceolate, acute tip, truncate base, surface with weak pubescence, margin entire.
- *Size of sepals.*—12–14 mm long, 4 mm wide for the largest upper sepal, 2–3 mm in width for the other sepals.

Bud (just prior to petals unfolding):
- *Shape.*—Elliptical.
- *Color of sepals.*—Light green, RHS 143 C.
- *Color of petals.*—Light pink, RHS 62 C.
- *Length.*—19 mm.
- *Width.*—11 mm.

Reproductive organs:
- *Androecium.*—7–9 fertile anthers, moderate pollen, yellow-orange, RHS 30 A, filaments white, RHS 155 D, to light-pink, RHS 52 D.
- *Gynoecium.*—One pistil, style and stigma pink, RHS 58 C, stigma 5–6-lobed.
- *Fertility/seed set.*—Occasionally weak seed set, mainly in late summer to fall.
- *Fruit.*—Oblong, about 6 mm wide, rostrum (beak) 38–42 mm long.
- *Seed.*—Oblong, 4–5 mm long, brown, RHS 177 B.

Spring flowering response period: In Hillscheid, Germany, in 2002 plants had on average 0.2 flowers opened 8 weeks after planting of rooted cuttings.

Outdoor flower production: Continuously and moderately rich flowering, the flower count in 2002 in Hillscheid, Germany, indicated about 3–3.5 inflorescence per plant in mid May, but increasing thereafter.

Durability: Good stability of flower color, good rain resistance.

Lastingness of the individual flower: About 7 days at 18° C., about 16–18 days for the umbel.

Fragrance: None.

PLANT

Foliage:
- *Shape.*—Kidney-shaped with weak lobes, cordate base with open gap between the lowest lobes.
- *Margin.*—Bicrenate, moderately wavy.
- *Texture.*—Upper surface smooth, velvety.
- *Size of leaf.*—120 mm wide, 70 mm long.
- *Color of upper surface.*—Medium green, approximately RHS 137 B.
- *Color of zonation.*—Darker green, about RHS 137 A, not always visible on mature leaves.
- *Color of lower surface.*—RHS 137 D.
- *Petioles.*—75–85 mm long, 3–4 mm diameter, light green in color, approximately RHS 143 C.

General appearance and form:
- *Stem color.*—Green, RHS 143 A.
- *Internode length.*—15–25 mm.
- *Branching pattern.*—5.8 branches.
- *Plant size.*—Height: 21.5 cm, width: 32.5 cm (10-week-old plants, as described, measured from the top of the soil (base of the main stem) to the surface of the foliage canopy without inflorescences).

Pest/Disease Resistance/Susceptibility: No observations to date.

I claim:

1. A new and distinct cultivar of geranium plant named 'Fip 336', as described and illustrated herein.

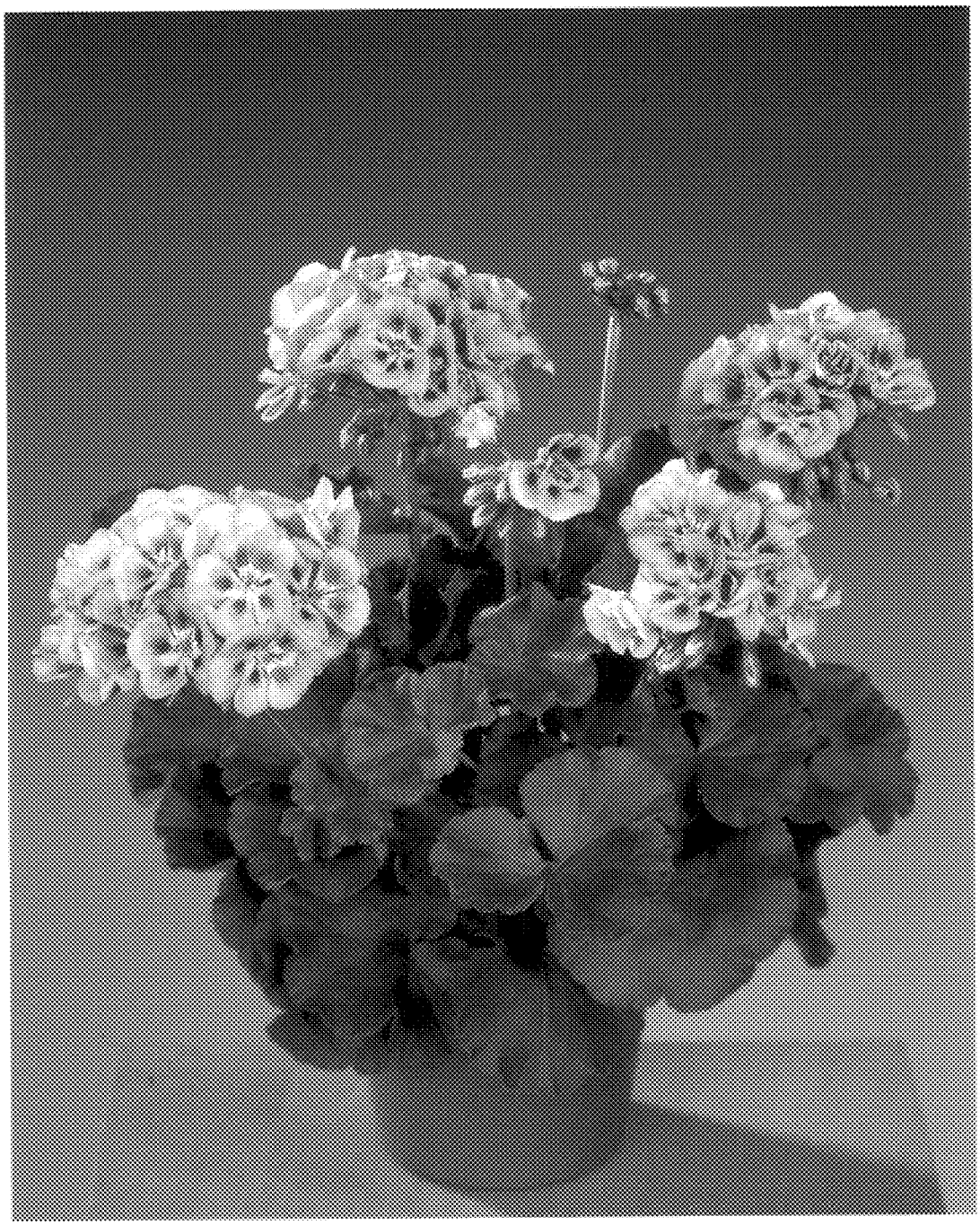

* * * * *